United States Patent
Jono et al.

(10) Patent No.: US 9,939,607 B2
(45) Date of Patent: Apr. 10, 2018

(54) LENS BARREL, IMAGE OBTAINING UNIT, AND METHOD FOR ASSEMBLING SAME

(71) Applicant: KONICA MINOLTA, INC., Chiyoda-ku (JP)

(72) Inventors: Junichi Jono, Kita-ku (JP); Yasuyuki Natsuno, Hachioji (JP); Yuichi Atarashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 312 days.

(21) Appl. No.: 14/650,216

(22) PCT Filed: Dec. 4, 2013

(86) PCT No.: PCT/JP2013/082562
§ 371 (c)(1),
(2) Date: Jun. 5, 2015

(87) PCT Pub. No.: WO2014/088024
PCT Pub. Date: Jun. 12, 2014

(65) Prior Publication Data
US 2015/0316742 A1  Nov. 5, 2015

(30) Foreign Application Priority Data
Dec. 5, 2012 (JP) .................................. 2012-265870

(51) Int. Cl.
*H04N 5/225* (2006.01)
*G02B 7/02* (2006.01)
(Continued)

(52) U.S. Cl.
CPC .......... *G02B 7/025* (2013.01); *A61B 1/00096* (2013.01); *A61B 1/05* (2013.01);
(Continued)

(58) Field of Classification Search
CPC ....... A61B 1/00096; A61B 1/05; A61B 1/055; B32B 2307/412; B32B 2551/00;
(Continued)

(56) References Cited

U.S. PATENT DOCUMENTS 5,376,983 A * 12/1994 Yamazaki ................ G02B 7/10
359/825
2007/0008407 A1 * 1/2007 Yamamoto ............... A61B 1/05
348/65

FOREIGN PATENT DOCUMENTS

JP 61-107307 5/1986
JP 61-107308 5/1986
(Continued)

*Primary Examiner* — Md Haque
(74) *Attorney, Agent, or Firm* — Cozen O'Connor

(57) ABSTRACT

A lens barrel for imaging a subject; and a lens frame which holds the lens. The lens frame includes a body structure opened at a tip and an end; and a lens base which fixes the lens and is adhered to a tip opening of the body; the lens base includes: a tip base including an opening which exposes a tip side lens optical surface and an inner side which supports the lens; and a circle or arc sidewall extending axially from the tip base; the inner surface of the sidewall is formed along an outer circumference surface of the lens; the inner side surface and the outer circumference are adhered to each other; and a portion of the upper surface of the sidewall is provided toward an end side separated from the far end of the lens to be exposed inside the body.

12 Claims, 10 Drawing Sheets

(51) Int. Cl.
*B32B 37/14* (2006.01)
*B32B 37/18* (2006.01)
*B32B 37/12* (2006.01)
*A61B 1/00* (2006.01)
*A61B 1/05* (2006.01)
*A61B 1/055* (2006.01)
*G02B 23/24* (2006.01)

(52) U.S. Cl.
CPC .............. *A61B 1/055* (2013.01); *B32B 37/12* (2013.01); *B32B 37/142* (2013.01); *B32B 37/18* (2013.01); *G02B 23/2476* (2013.01); *H04N 5/2253* (2013.01); *H04N 5/2254* (2013.01); *B32B 2307/412* (2013.01); *B32B 2551/00* (2013.01); *H04N 5/2257* (2013.01); *H04N 2005/2255* (2013.01)

(58) Field of Classification Search
CPC ....... B32B 37/12; B32B 37/142; B32B 37/18; G02B 23/2476; G02B 7/025; H04N 2005/2255; H04N 5/2253; H04N 5/2254; H04N 5/2257
See application file for complete search history.

(56) References Cited

FOREIGN PATENT DOCUMENTS

| | | | |
|---|---|---|---|
| JP | 61-107310 | | 5/1986 |
| JP | 2-66506 | | 3/1990 |
| JP | 7-5352 | | 1/1995 |
| JP | 8-194171 | | 7/1996 |
| JP | 2000-162508 | | 6/2000 |
| JP | 2000162508 | * | 6/2000 |
| JP | 2002-95626 | | 4/2002 |
| JP | 2005-227728 | | 8/2005 |
| JP | 2012-2943 | | 1/2012 |
| WO | WO 2008/035470 | | 3/2008 |

* cited by examiner

LENS BARREL, IMAGE OBTAINING UNIT, AND METHOD FOR ASSEMBLING SAME

RELATED APPLICATIONS

This is a U.S. National Phase Application under 35 USC 371 of International Application PCT/JP2013/082562 filed on Dec. 4, 2013.

This application claims the priority of Japanese application no. 2012-265870 filed Dec. 5, 2012, the entire content of which is hereby incorporated by reference.

TECHNICAL FIELD

The present invention relates to a lens barrel, an image obtaining unit, and an assembling method of the above. Specifically, the present invention relates to a lens barrel and an image obtaining unit composing a small diameter endoscope and an assembling method of the above.

BACKGROUND ART

In a typical camera lens barrel, an outer diameter of the lens is relatively large. Therefore, the flange portion of the lens is held with tweezers and the lens is dropped into the lens frame to manufacture the lens barrel. Instead of using tweezers, air is sucked to adsorb the lens with an adsorption pad to hold the lens.

In a lens barrel composing a tip portion of an endoscope with a small diameter of about 1 mm, when the lens frame is a small diameter or the lens frame is long in an optical axis direction (therefore, the lens inserting hole is deep), it is difficult to insert the lens. Undoubtedly, using tweezers to hold such a very small lens is very difficult, and accurately inserting the lens into the lens frame by free fall is also very difficult.

An endoscope is used to be inserted in a live body lumen to observe live body tissue. As a structure of a tip of the endoscope, there is a structure providing a lens which images an image of an object of an observation target and an imaging element or an imaging fiber such as a CCD (charge coupled device) in which the image is input. When the imaging element is used, an image signal converted to an electric signal with the imaging element is transmitted outside the body with a transmitting cable, and when the imaging fiber is used, the image is transmitted outside the body with the imaging fiber as is, and after going through the image processing apparatus, the image can be displayed and observed on the image display apparatus.

As described in patent literature 1 to 5, the lens is positioned inside the lens frame and the outer circumferential portion of the lens is adhered to the inner circumferential surface of the lens frame to fix the units in order to include the lens in the optical device. When the lens is fixed with adhesive, it is important that a sufficient amount of adhesive can be filled in the necessary portion and that the adhesive is not attached to the optical surface of the lens so that there is no bad influence to the optical performance.

According to patent literature 1 to 3, a ring shaped groove is provided to prevent the adhesive from flowing out to the effective face of the lens. The ring shaped groove is provided in the lens and one or both holding planes.

According to patent literature 4, in order to prevent the lens from rising in the thrust direction, a tapered portion is provided in the lens or the inner circumferential portion of the frame and the portion is filled with adhesive. The hardening shrinkage of the adhesive causes pulling force in the thrust direction.

According to patent literature 5, a through hole is provided to insert adhesive in a gap between the lens supporting frame and the lens circumferential surface.

Patent literature 6 and 7 describe a tip structure of an endoscope in which the lens and the imaging fiber are positioned on the same axis and fixed with a cylinder shaped frame.

PRIOR ART DOCUMENT

Patent Literature

Patent Literature 1: Japanese Patent Application Laid-Open Publication No. S61-107307
Patent Literature 2: Japanese Patent Application Laid-Open Publication No. S61-107308
Patent Literature 3: Japanese Patent Application Laid-Open Publication No. S61-107310
Patent Literature 4: Japanese Patent Application Laid-Open Publication No. H02-066506
Patent Literature 5: Japanese Patent Application Laid-Open Publication No. H07-005352
Patent Literature 6: Japanese Patent Application Laid-Open Publication No. H08-194171
Patent Literature 7: Japanese Patent Application Laid-Open Publication No. 2000-162508

SUMMARY OF INVENTION

Problems to be Solved by the Invention

In order to reduce the burden of the subject, it is preferable that the endoscope is made with a small diameter. Moreover, the endoscope inserted in a fallopian tube, a bile duct, a pancreatic duct or the like needs to be a very small diameter of about 1 mm or less.

When the lens holding structure as described in patent literature 1 to 5 is employed as the tip structure of the endoscope, the process of sufficiently filling the adhesive to the necessary portion and filling the adhesive so that there is no bad influence to the optical performance such as preventing adhesive from being attached to the optical surface of the lens becomes difficult as the diameter of the endoscope becomes smaller.

As described in patent literature 6 and 7, a lens frame to position the image input surface of the imaging element or the imaging fiber with respect to the lens and to hold the above is provided in the tip structure of the endoscope including the lens and the imaging element or imaging fiber. It is desired that not only the lens but also the imaging element or the imaging fiber can be fixed with the same lens frame and the above can be assembled accurately.

When an attempt is made to make the diameter of the tip structure of the endoscope smaller, the lens should be made with a small diameter. However, there is a needs to make the effective diameter where optical surface of the lens is formed as large as possible from the viewpoint of the performance of the endoscope. In other words, there is a needs to make the flange portion outside the effective diameter of the lens as small as possible. However, when a lens hardly having a flange portion outside the effective diameter with a very small diameter within the very small diameter of about 1 mm or smaller is manufactured by injection molding, the process of removing a gate edge becomes relatively difficult. In such case, if the structure can be used with the gate edge remaining, the manufacturing of the lens becomes easy.

The present invention has been made in view of the above problems of the conventional technique, and an object of the present invention is to provide a lens barrel, an image obtaining unit and an assembly method of the above in which even if the lens barrel is long and has a small diameter, the adhesive can be filled in suitable places to maintain airtightness and watertightness and the above can be easily assembled accurately.

Means for Solving the Problem

In order to solve the above-described problems, the invention according to Aspect 1 provides a lens barrel including:
a lens which images an image of a subject; and
a lens frame which holds the lens inside,
wherein,
the lens frame includes:
a cylinder body component with a structure opened at a tip and an end; and
a lens base component which fixes the lens and which is adhered and fixed to a tip opening of the cylinder body component to store the lens inside the cylinder body component;
the lens base component includes:
a tip base portion including an opening which exposes a tip side optical surface of the lens and an inner side surface which supports the lens in a surrounding portion of the opening; and
a full circle or arc shaped side wall portion provided standing from the tip base portion in an axis direction;
the inner side surface of the side wall portion is formed along an outer circumferential surface of the lens;
the inner side surface and the outer circumferential surface are brought together and adhered to each other;
at least a portion of the upper surface of the side wall portion is provided in a position toward an end side separated from the far end of the lens to be exposed to the inside of the cylinder body component, comes into contact with a tip surface edge of a member with a larger diameter than the lens inserted from an end opening of the cylinder body component, and composes a positioning surface to determine a position of an axis direction of the member; and
the lens is provided in a position shifted from a central axis of an inserting portion in which the member of the cylinder body component is inserted and the positioning surface is provided in a side opposite of the side that the lens is shifted.

According to Aspect 2, in the lens barrel of Aspect 1, the side wall portion is formed in an arc shape in which a portion on the side that the lens is shifted is missing.

According to Aspect 3, in the lens barrel of Aspect 1 or 2,
the side wall portion is inserted in the cylinder body component;
the outer side surface of the side wall portion is formed along an inner circumferential surface of the cylinder body component; and
the outer side surface and the inner circumferential surface are brought together and adhered to each other.

According to Aspect 4, in the lens barrel of Aspect 3,
the tip base portion includes a flange portion projecting outward from the side wall portion in a radial direction in an outer circumferential portion; and
the flange portion is in contact with a tip surface of the cylinder body component in a full circle.

According to Aspect 5, in the lens barrel of Aspect 3 or 4,
a groove is formed in an outer side surface of the side wall portion, and the outer side surface is adhered to an inner circumferential surface of the cylinder body component by adhesive filled in the groove.

According to Aspect 6, in the lens barrel of Aspect 1 or 2,
a cutout portion is formed cutting out the cylinder body component from a tip surface; and
the side wall portion fits into the cutout portion to close the cutout portion.

According to Aspect 7, in the lens barrel of any one of Aspects 1 to 6,
a groove is formed in a portion surrounding a portion which supports a tip surface of the lens of an inner side surface of the tip base portion in a full circle, and the lens is fixed to the tip base portion by adhesive filled in the groove.

According to Aspect 8, in the lens barrel of any one of Aspects 1 to 7, a through hole is formed on the side wall portion to go through to the inner side surface of the side wall portion, the inner side surface in contact with the outer circumferential surface of the lens.

According to Aspect 9, in the lens barrel of any one of Aspects 1 to 8, a gate edge formed in injection molding of the lens is left projecting from an outer circumferential surface of the lens, and a groove to store the gate edge is formed in the side wall portion.

According to Aspect 10, an image obtaining unit includes:
a lens barrel of any one of Aspects 1 to 9,
wherein, an imaging unit or an imaging fiber is inserted in the cylinder body component as the member, the imaging unit or the imaging fiber with an image input surface where an image imaged by the lens is input provided in a tip surface; and
the imaging unit or the imaging fiber is held so that an outer circumferential surface is in contact with an inner circumferential surface of the cylinder body component in a full circle, and a tip surface edge comes into contact with the positioning surface to hold an interval with the lens in an axis direction.

According to Aspect 11, a method for assembling a lens barrel according to any one of Aspects 1 to 9, includes:
adhering and fixing the lens to the lens base component; and
after the above, adhering and fixing the lens base component to the cylinder body component.

According to Aspect 12, a method for assembling an image obtaining unit according to Aspect 10, includes:
adhering and fixing the lens to the lens base component, and then adhering and fixing the lens base component to the cylinder body component;
after the above, inserting the imaging unit or the imaging fiber in the cylinder body component and fixing the cylinder body component in a state where the tip surface edge is in contact with the positioning surface.

Advantageous Effects of Invention

According to the present invention, the lens frame which holds the lens inside is divided between a cylinder body component and a lens base component. Therefore, there is no need to drop the lens in the lens frame. First, the lens is adhered and fixed to the lens base component and then the lens base component is adhered and fixed to the cylinder body component. With this, the components can be easily assembled.

A tip surface of the lens is comfortably supported by the inner side surface of the tip base portion, and the outer circumferential surface is matched with the inner side surface of a side wall portion to be accurately positioned.

Since the lens base component is divided from the cylinder body component, the lens base component is not so long. When the side wall portion is in a full circle shape, the hole is not too deep, and when the side wall portion is formed in an arc shape, the structure is not a hole surrounding the lens. Therefore, it is easy to accurately position the lens in the lens base component. Moreover, the following process becomes easy to perform, to confirm whether the adhesive is suitably spread in a suitable amount, to accurately temporarily fix the lens with the lens base component in the hardening process of the adhesive, and to test the accuracy of the fixed position and the sealing performance after the adhesive hardens.

At least a portion of the upper surface of the side wall portion composes a positioning surface and positions the axis direction position of the imaging unit or the imaging fiber inserted from the end opening of the cylinder body component.

The lens is provided in a position shifted from the central axis of the inserting portion where the member of the cylinder body component is inserted, and the positioning surface of the upper surface of the side wall portion is shifted to the opposite side that the lens is shifted. Therefore, the thickness of the side wall portion to the shifted side, that is, the hardness of the side wall portion and the necessary width of the positioning surface can be secured while suppressing the occupying rate of the side wall portion in the radial direction to a low value. Since the necessary width of the positioning surface is secured, the imaging unit or the imaging fiber can be reliably latched. Since the hardness of the side wall portion is secured, the accuracy of positioning the lens and the imaging unit or the imaging fiber is highly secured. Since the occupying rate of the side wall portion in the radial direction is low, the small diameter of the lens barrel can be easily maintained and enhanced.

Therefore, according to the present invention, even if the lens barrel is long and has a small diameter, the adhesive can be filled in the suitable position, the airtightness and the watertightness can be secured, and the configuration can be easily assembled.

By using the above, an image obtaining unit to be inserted in a small path to observe inside, specifically, since there is airtightness and watertightness, an endoscope with a small diameter for live body observation to be inserted in a fallopian tube, a bile duct, a pancreatic duct or the like so as to be able to observe inside can be made with good yield rate and low costs.

BRIEF DESCRIPTION OF DRAWINGS

FIG. 5B is a perspective view of a lens and a lens base component combined with the diaphragm plate of the additional example of the present invention in between.

EMBODIMENT FOR CARRYING OUT THE INVENTION

An embodiment of the present invention is described below with reference to the drawings. Described below is one embodiment of the present invention and does not limit the present invention.

First Embodiment

First, the first embodiment of the present invention is described.

Figure 1:
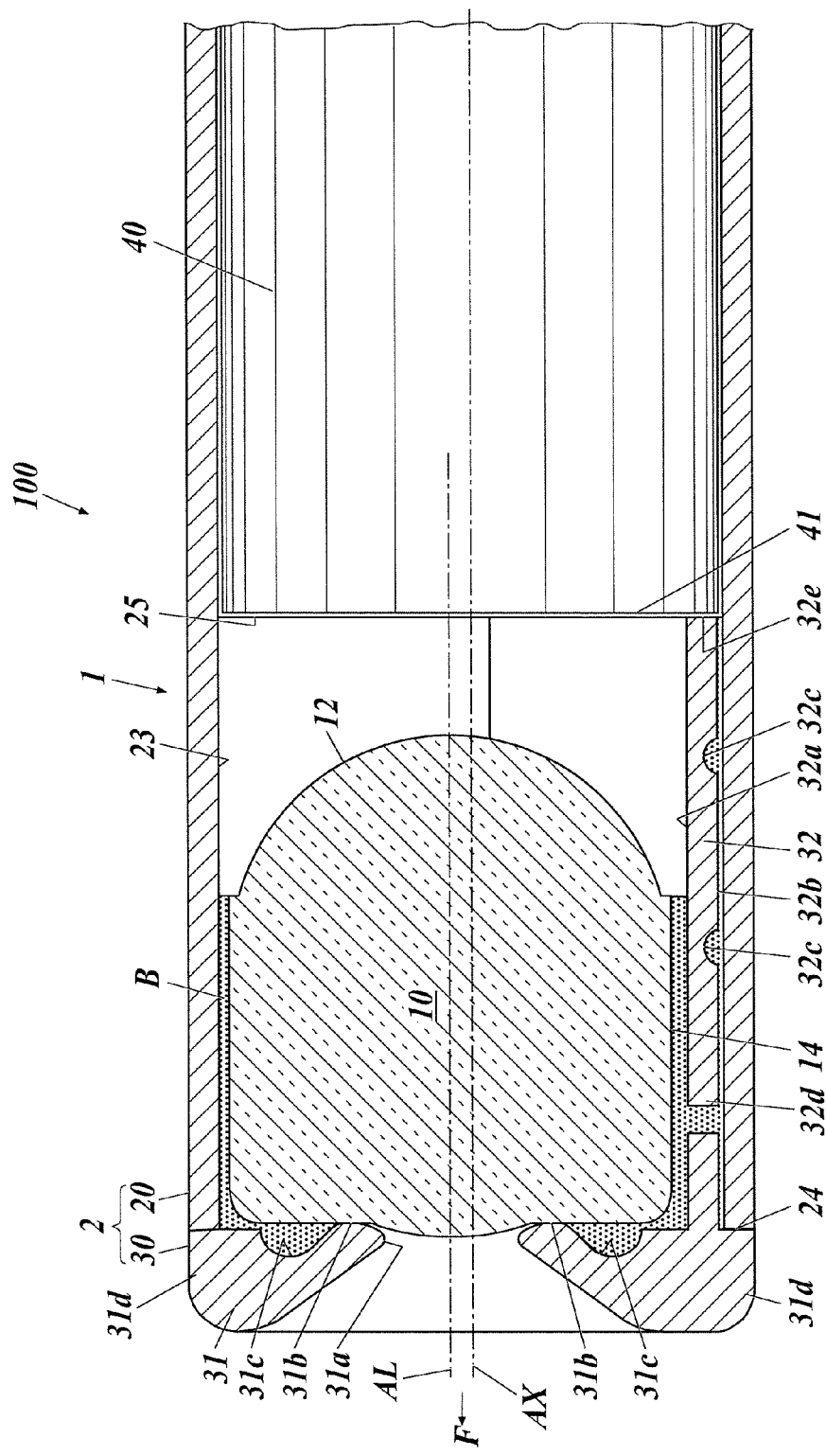
FIG. 1 is a longitudinal section view of a tip portion of an image obtaining unit including a lens barrel of a first embodiment of the present invention.
Figure 2:
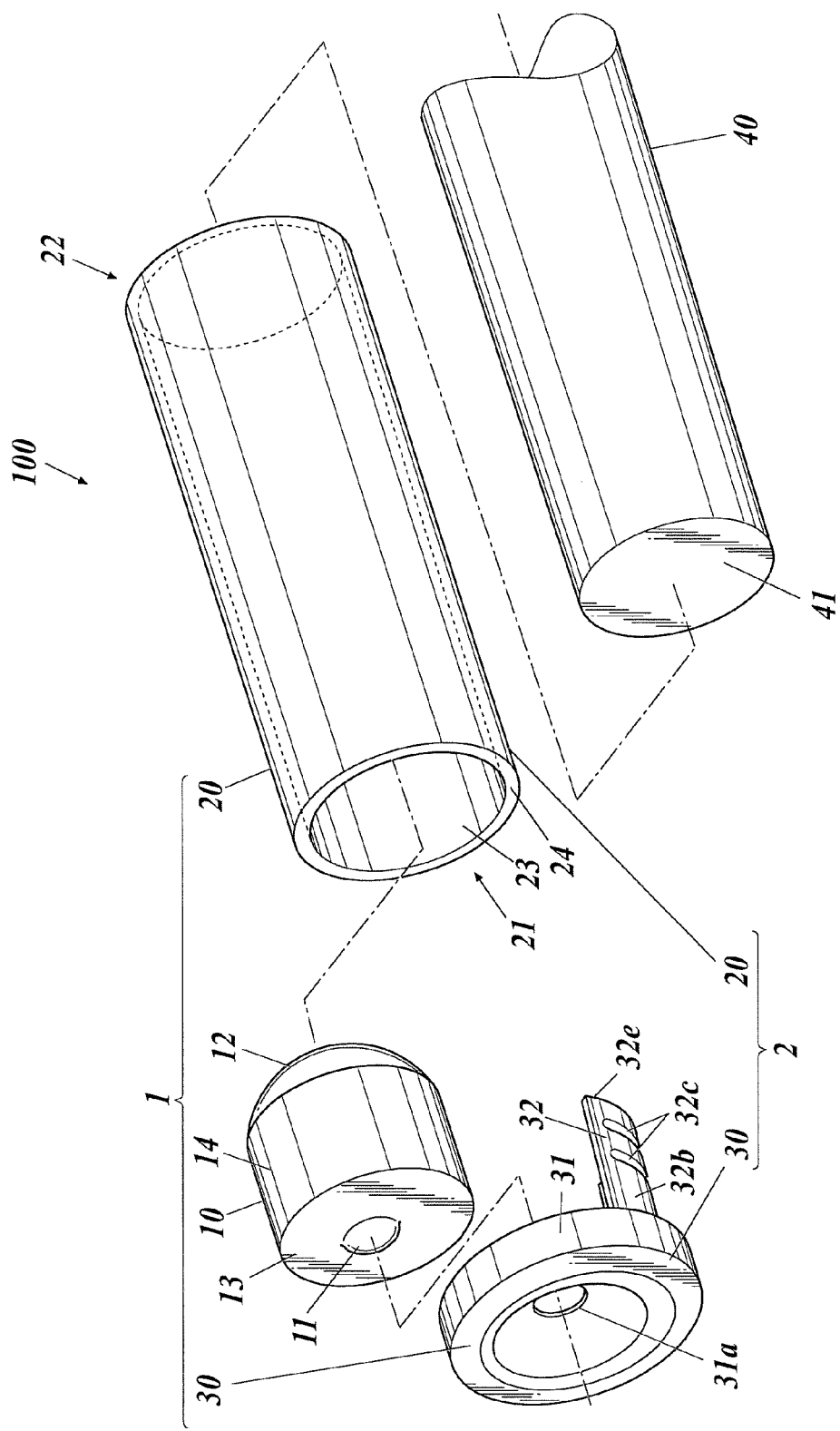
FIG. 2 is an exploded perspective view of the image obtaining unit including the lens barrel of the first embodiment of the present invention.

As shown in FIG. 1 and FIG. 2, an image obtaining unit 100 is composed by attaching a lens barrel 1 to a tip portion of an imaging unit or imaging fiber 40. The lens barrel 1 includes a lens 10 which images an image of a subject, and a lens frame 2 which holds the lens 10 inside. The lens frame 2 includes a cylinder body component 20 and a lens base component 30 assembled together. In the lens barrel 1 and the image obtaining unit 100, the side where the lens 10 is provided is to be a tip and the opposite side is to be an end. B in the figure shows adhesive and arrow F shows a tip direction.

The lens 10 includes a tip side optical surface 11 and an end side optical surface 12. The lens 10 is a resin lens formed by injection molding with the end side optical surface 12 being the concave lens surface. Any lens surface with a convex shape, a concave shape or a planar shape can be applied for the tip side optical surface 11. The tip side optical surface 11 is positioned in the tip direction F, and faces an object to be observed. The end side optical surface 12 is positioned in an end direction and faces a tip surface 41 of the imaging unit or the imaging fiber 40. The effective diameter of the tip side optical surface 11 is to be $\varphi 1$, and the effective diameter of the end side optical surface 12 is to be $\varphi 2$. $\varphi 1 < \varphi 2$, and the tip surface 13 outside the effective diameter φ1 is to be larger than the end surface (no reference numeral) outside the effective diameter φ2. The lens 10 includes the outer circumferential surface 14 formed in a circumferential shape of a right circular cylinder.

The cylinder body component 20 is a cylinder shape with both edges open. In other words, the cylinder body component 20 has a structure in which the tip and the end are open, and a tip opening 21 and an end opening 22 are formed. The inner circumferential surface 23 of the cylinder body component 20 is formed with a certain inner diameter larger than the outer diameter of the lens 10 in at least the inserting portion (including from end opening 22) in which the imaging unit or the imaging fiber 40 is inserted and a central axis AX is in a straight line. The central axis AL of the lens 10 is shifted from the central axis AX. Reference numeral 24 shown in FIG. 2 represents the tip surface of the cylinder body component 20. The shape of the outer circumferential surface of the cylinder body component 20 can be chosen freely. For simplicity, an outer circumferential surface concentric to the inner circumferential surface 23 is shown. According to the present embodiment, the axis AX is the central axis of the entire image obtaining unit 100.

Figure 3:
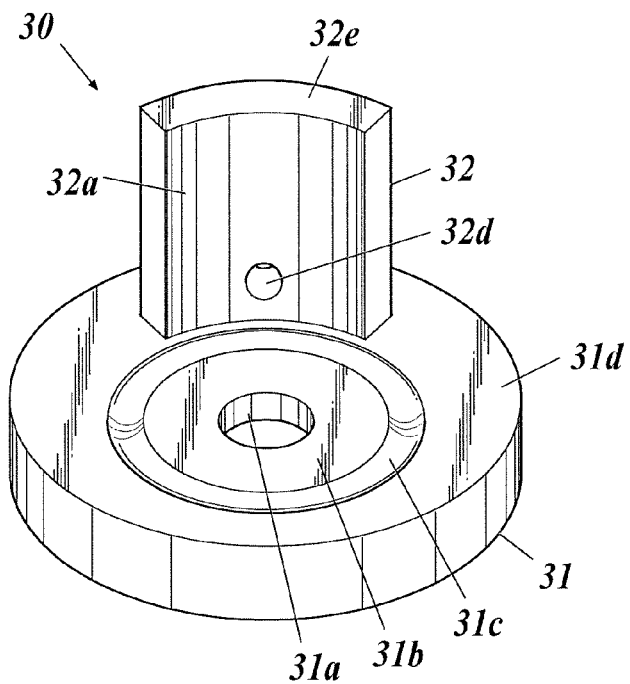
FIG. 3 is a perspective view of a lens base component of the first embodiment of the present invention viewed from a direction different from FIG. 2.

As shown in FIG. 1, FIG. 2, and FIG. 3, the lens base component 30 includes a tip base portion 31 and an arc shaped side wall portion 32.

The tip base portion 31 includes an opening 31a which exposes the tip side optical surface 11 of the lens 10. The outer diameter of the tip base portion 31 is formed with the central axis AX as the center, but the opening 31a is formed with the central axis AL as the center to expose the tip side optical surface 11.

A tip circumferential contact portion 31b which comes into contact with the tip surface 13 of the lens 10 in a full circle is formed around the opening 31a on the inner side surface of the tip base portion 31. The tip circumferential contact portion 31b is the inner side surface which supports the lens 10. The tip circumferential contact portion 31b supports the tip surface 13 of the lens 10 in a full circle and comes into contact with the tip surface 13 in a full circle since there is no component which comes between the lens 10 in the present embodiment. The tip circumferential contact portion 31b is formed with the central axis AL as the center and is in a surface perpendicular to the central axis AL.

A groove 31c for filling adhesive around the tip circumferential contact portion 31b is formed in a full circle on the inner side surface of the tip base portion 31.

The tip base portion 31 includes a flange portion 31d projecting outward in the radial direction from the arc shaped side wall portion 32 in the outer circumferential portion.

The arc shaped side wall portion 32 is a portion provided standing in the axis AL direction from the tip base portion 31. The arc shaped side wall portion 32 is provided shifted from the central axis AL in the direction of the central axis AX. The arc shaped side wall portion 32 is provided limited to the range less than 180 degrees with the central axis AL as the center and is formed in an arc shape with the remaining range missing. The range is set to less than 180 degrees to make the lens 10 easy to put in and can be formed to be 180 degrees or larger.

The inner side surface 32a of the arc shaped side wall portion 32 is formed along the outer circumferential surface 14 of the lens 10. In other words, the inner side surface 32a is formed in an arc shape with the central axis AL as the center. The arc shaped side wall portion 32 is inserted in the cylinder body component 20. The lens frame 2 is composed so that the end surface of the flange portion 31d is in contact with the tip surface 24 of the cylinder body component 20 in a full circle.

The outer side surface 32b of the arc shaped side wall potion 32 is formed along the inner circumferential surface 23 of the cylinder body component 20. In other words, the outer side surface 32b is formed in an arc shape with the central axis AX as the center. A groove 32c for filling the adhesive is formed in the outer side surface 32b of the arc shaped side wall portion 32. The number of grooves 32c and the direction is not limited. The diagrams illustrate the groove 32c formed in the circumferential direction with the central axis AX as the center. However, the groove 32c can be formed in a diagonal direction, or a direction parallel to the central axis AX, or formed in a curve shape.

A through hole 32d is formed in the arc shaped side wall portion 32. The through hole 32d is formed through the arc shaped side wall portion 32 in the thickness direction and connects the inner side surface 32a of the arc shaped side wall portion 32 with the outer side surface 32b. Specifically, the through hole 32d is open and connects to the inner circumferential surface of the inner side surface 32a in contact with the outer circumferential surface 14 of the lens 10.

The upper surface 32e of the arc shaped side wall portion 32 is provided in a position separated to the end side than the far end of the lens 10 (vertex of end side optical surface 12). With this, since the arc shaped side wall portion 32 is inserted in the internal space surrounded by the inner circumferential surface 23 of the cylinder body component 20, the upper surface 32e is exposed to the inside of the cylinder body component. The upper surface 32e includes a positioning surface to position the axis AX direction position of the tip surface 41 of the imaging unit or the imaging fiber 40. According to the present embodiment, the entire upper surface 32e is the positioning surface.

The lens base component 30 includes the above, and the lens 10 is adhered and fixed. The lens 10 is adhered and fixed to the tip opening 21 of the cylinder body component 20 to store the lens 10 inside the cylinder body component 20. The lens 10 is provided in a position shifted from the central axis AX of the inserting portion where the imaging unit or the imaging fiber 40 of the cylinder body component 20 is inserted. The arc shaped side wall portion 32 and its upper surface 32e is shifted to the opposite of the side to which the lens 10 is shifted.

The imaging unit or the imaging fiber 40 is a component with a larger diameter than the lens. The outer diameter of the imaging unit or the imaging fiber 40 is a diameter so that the outer circumferential surface can be in contact with the inner circumferential surface 23 of the cylinder body component 20 in a full circle while being able to insert the imaging unit or the imaging fiber 40 in the cylinder body component 20 to be held by the inner circumferential surface 23. Therefore, the central axis of the imaging unit or the imaging fiber 40 is the same as the central axis AX of the inner circumferential surface 23.

When the member 40 is an imaging unit, the image input surface of the imaging element such as the CCD is positioned in the tip surface 41, and the image imaged by the lens 10 is input to the image input surface to be converted to the electric signal. Although not shown, an image transferring cable is extended out to the end direction from the substrate where the imaging element is loaded. When the member 40 is an imaging fiber, the image entering edge surface (image input surface) is provided in the tip surface 41 and the image imaged by the lens 10 is input to the image entering edge surface.

The upper surface 32e of the arc shaped side wall portion 32 comes into contact with the edge portion of the tip surface 41 of the imaging unit or the imaging fiber 40. With this, the interval between the imaging unit or the imaging fiber 40 and the lens 10 in the axis direction can be maintained and this composes the image obtaining unit 100. According to the present embodiment, since the entire upper surface 32e is the positioning surface, the upper surface 32e is on a surface perpendicular to the axis AX so as to be in contact with the tip surface 41 by the surface.

As shown in FIG. 1, the inner side surface 32a of the arc shaped side wall portion 32 is brought together with the outer circumferential surface 14 of the lens 10 and adhered to each other with the adhesive B. Moreover, the outer side surface 32b of the arc shaped side wall portion 32 is brought together with the inner circumferential surface 23 of the cylinder body component 20 and adhered to each other with the adhesive B. The outer side surface 32b is adhered to the inner circumferential surface 23 of the cylinder body component 20 with the adhesive B filled in the groove 32c. With this, the tip opening 21 of the cylinder body component 20 and the lens base component 30 are sealed together with high airtightness and watertightness by the adhesive B.

The tip surface 13 of the lens 10 is adhered to the tip base portion 31 by the adhesive B filled in the groove 31c. With this, the lens base component surrounding the opening 31a and the lens 10 are sealed together with high airtightness and watertightness by the adhesive B.

As described above, the tip opening 21 is sealed with the adhesive B and the lens base component 30 is closed with the lens 10. Therefore, the structure is airtight and watertight and can be used in the endoscope.

Next, the method of assembling the image obtaining unit 100 (including the lens barrel 1) of the first embodiment of the present invention is described.

Figure 4:
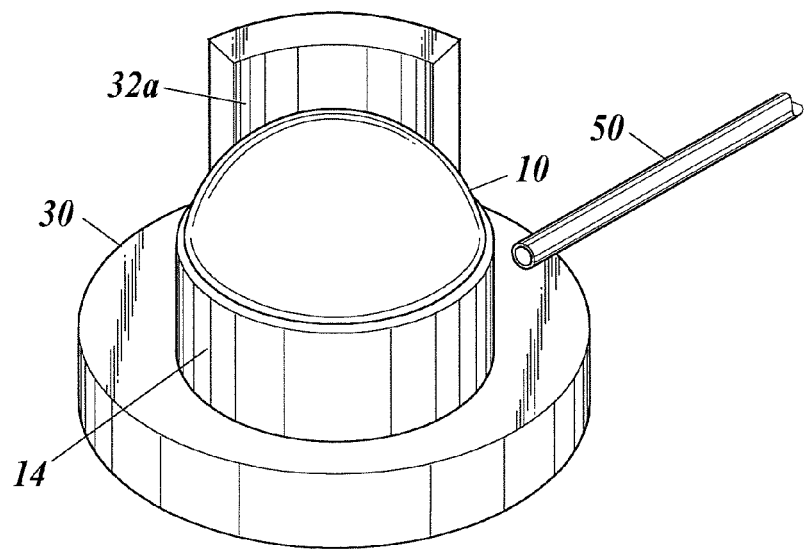
FIG. 4 is a perspective view showing a process of adhering a lens to the lens base component of the first embodiment of the present invention.

First, as shown in FIG. 4, a lens 10 is provided on the lens base component 30. A certain amount of adhesive is emitted from the nozzle 50 of the adhesive dispenser, and the adhesive is flown around in the groove 31c and between the outer circumferential surface 14 of the lens 10 and the inner side surface 32a of the arc shaped side wall portion 32, and the adhesive is hardened to adhere and fix the lens 10 to the lens base component 30.

The adhesive can be filled from the through hole 32d and around the space between the outer circumferential surface 14 and the inner side surface 32a to the groove 31c.

Figure 5A:
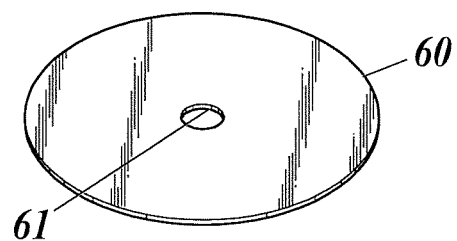
FIG. 5A is a perspective view of a diaphragm plate of an additional example of the present invention.
Figure 5B:
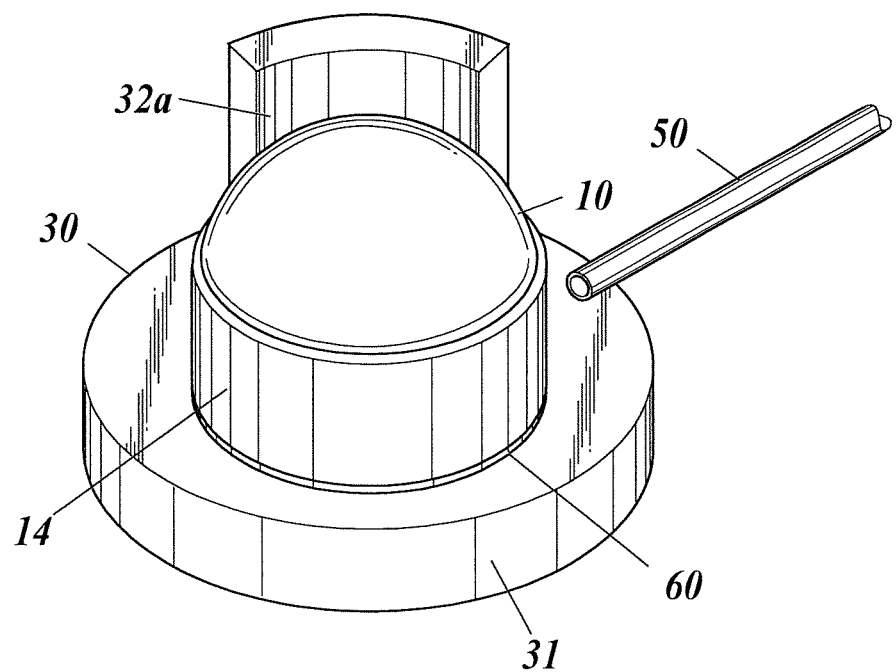

When it is not possible to form the opening 31a small enough due to the situation of manufacturing the lens base component 30, a diaphragm plate 60 punched with a pin hole 61 as shown in FIG. 5A can be provided between the lens 10 and the tip base portion 31 as shown in FIG. 5B. In this case, one surface of the diaphragm plate 60 is adhered to the tip surface 13 of the lens 10 and the opposite surface is in contact with the tip contact portion 31b in a full circle, and with this, is adhered to the tip base portion 31.

Then, adhesive is applied to suitable places of the portions of the outer side surface 32b of the arc shaped side wall portion 32 and the portion of the outer circumference surface 14 of the lens 10 which is not covered by the arc shaped side wall portion 32. Here, the groove 32c is filled with adhesive. The adhesive easily stays due to the groove 32c. Since the groove 32c is formed, the area of adhesion increases and therefore, the bonding strength after adhesion becomes high. A groove can be formed in the outer circumferential surface 14 of the lens 10 for the same purpose. After the adhesive is applied, the lens base component 30 is connected to the tip opening 21 of the cylinder body component 20 so that the lens 10 and the arc shaped side wall portion 32 is inserted inside, the adhesive is hardened to adhere and fix the lens base component 30 to the cylinder body component 20, and the fixed state by the adhesive B as shown in FIG. 1 is obtained.

Then, the tip of the imaging unit or the imaging fiber 40 is inserted from the end opening 22 of the cylinder body component 20 so that the edge portion of the tip surface 41 comes into contact with the upper surface 32e which is the positioning surface as described in FIG. 1, and the cylinder body component 20 is fixed in this state. According to such fixing method, adhesion with adhesive (not shown) filled between the inner circumferential surface 23 is enough.

Figure 6:
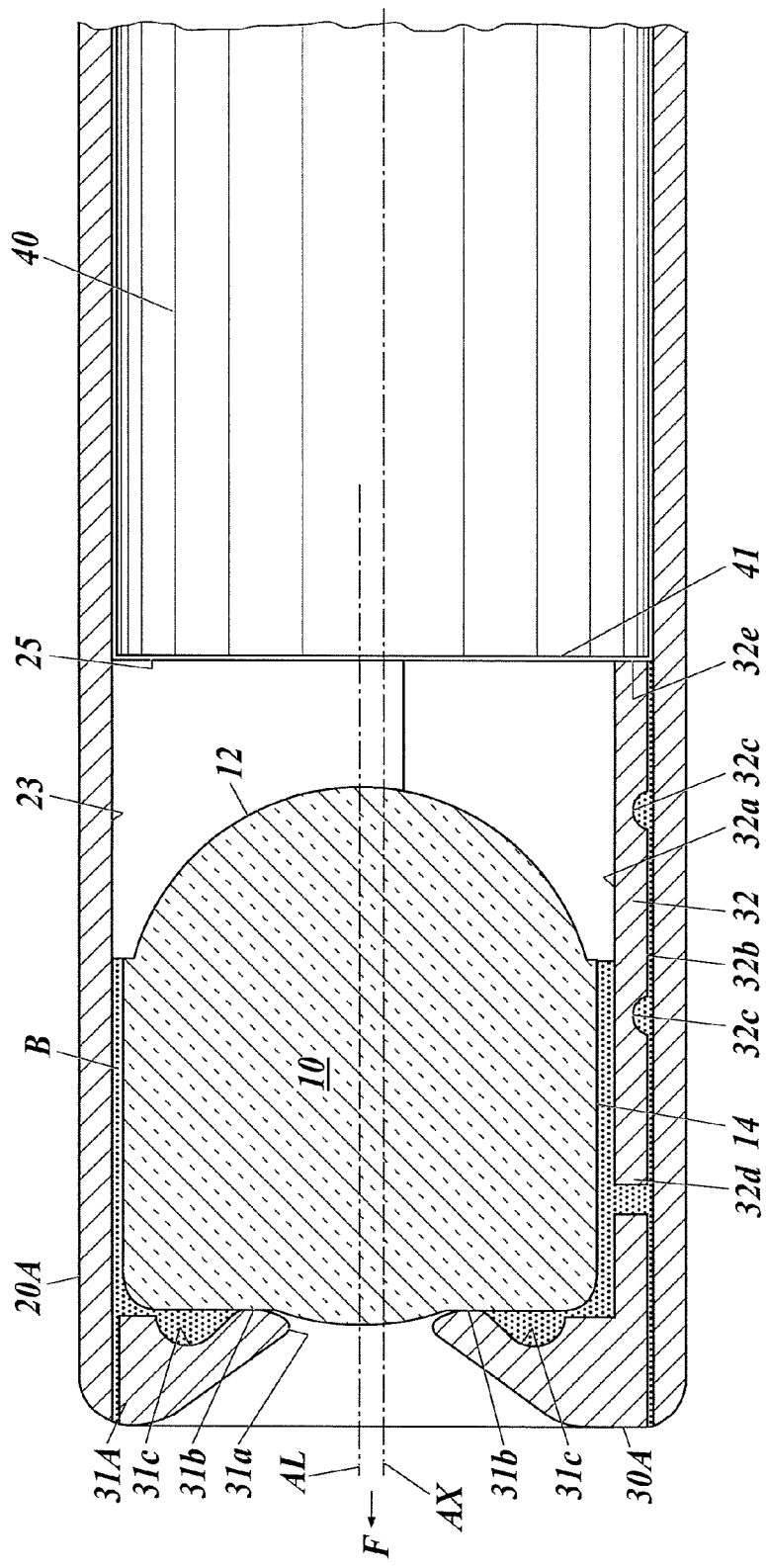
FIG. 6 is a longitudinal sectional view of the tip portion of the image obtaining unit including the lens barrel showing an example in which a flange portion is not provided in the lens base component according to an embodiment of the present invention.

As shown in the tip base portion 31A of the lens base component 30A shown in FIG. 6, the flange portion 31d does not have to be provided and the outer circumferential surface of the tip base portion 31A can be adhered to the inner circumferential surface 23 of the cylinder body component 20A. This structure can be similarly applied to the embodiment described below. However, it is preferable to provide the flange portion 31d to enhance the breaking strength from the burden of outside pressure.

Second Embodiment

Next, the second embodiment of the present invention is described.

According to the first embodiment, the arc shaped side wall portion 32 is employed as the lens base component 30.

Figure 7:
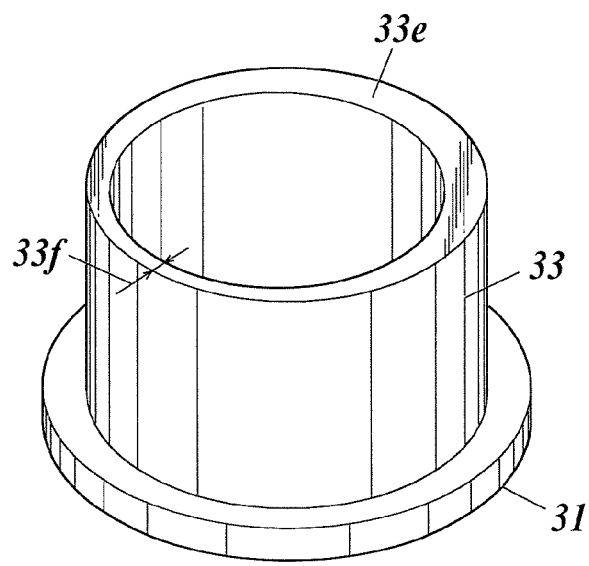
FIG. 7 is a perspective view of the lens base component applied in the second embodiment of the present invention.

According to the present embodiment, as shown in FIG. 7, a full circle side wall portion 33 is employed as the lens base component.

The lens 10 is shifted from the central axis AX and the upper surface 33e which is the positioning surface is shifted to the opposite side that the lens 10 is shifted. Therefore, there is a thinnest portion 33f to the side where the lens 10 is shifted. The lens barrel tends to become larger because it is difficult to form the thinnest portion 33f thinner and more accurately, and the full circle side wall portion 33 is provided in a full circle of the outer circle of the lens 10 inside the cylinder body component 20. Moreover, it is advantageous from the point of assembly, filling adhesive and testing to open around the lens 10 180 degrees or more as in the arc shaped side wall portion 32 of the first embodiment.

However, according to the present embodiment, compared to the lens frame in which the portions corresponding to the cylinder body component 20 and the lens base component 30 are made as one, it is advantageous from the point of ease of embedding the lens, filling the adhesive and testing of the lens frame.

Third Embodiment

Next, the third embodiment of the present invention is described.

Figure 8:
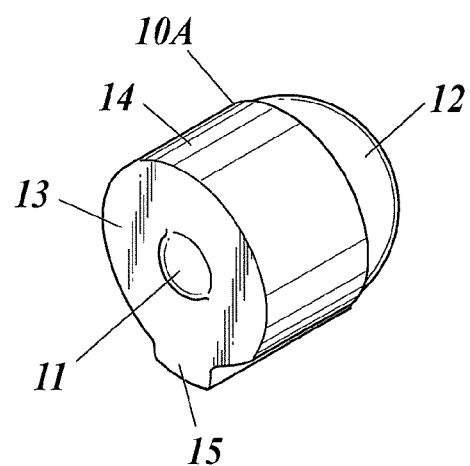
FIG. 8 is a perspective view of the lens applied in the third embodiment of the present invention.

The present embodiment is an embodiment which employs the lens 10A with a gate edge 15, formed when the lens is formed by injection molding, left projecting from the outer circumferential surface 14 as shown in FIG. 8.

Figure 9A:
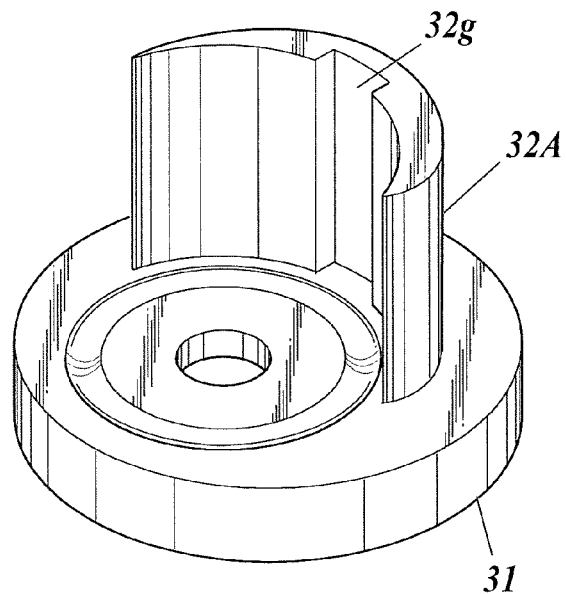
FIG. 9A is a perspective view of the lens base component applied in the third embodiment of the present invention and shows a bottom of the vertical groove remaining.
Figure 9B:
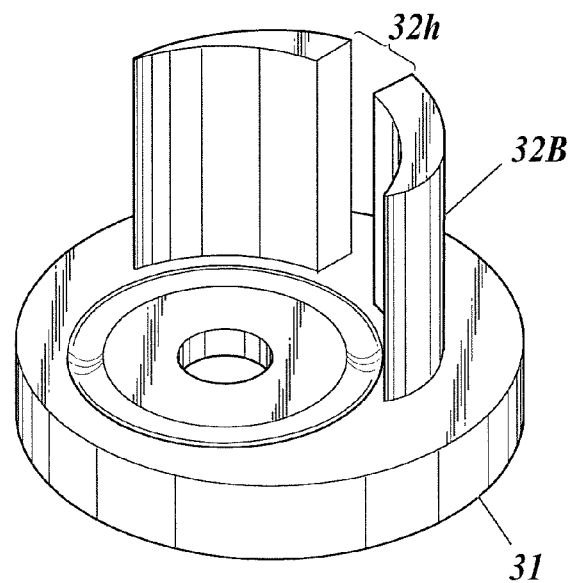
FIG. 9B is a perspective view of the lens base component applied in the third embodiment of the present invention and shows the bottom of the vertical groove not remaining.
Figure 10:
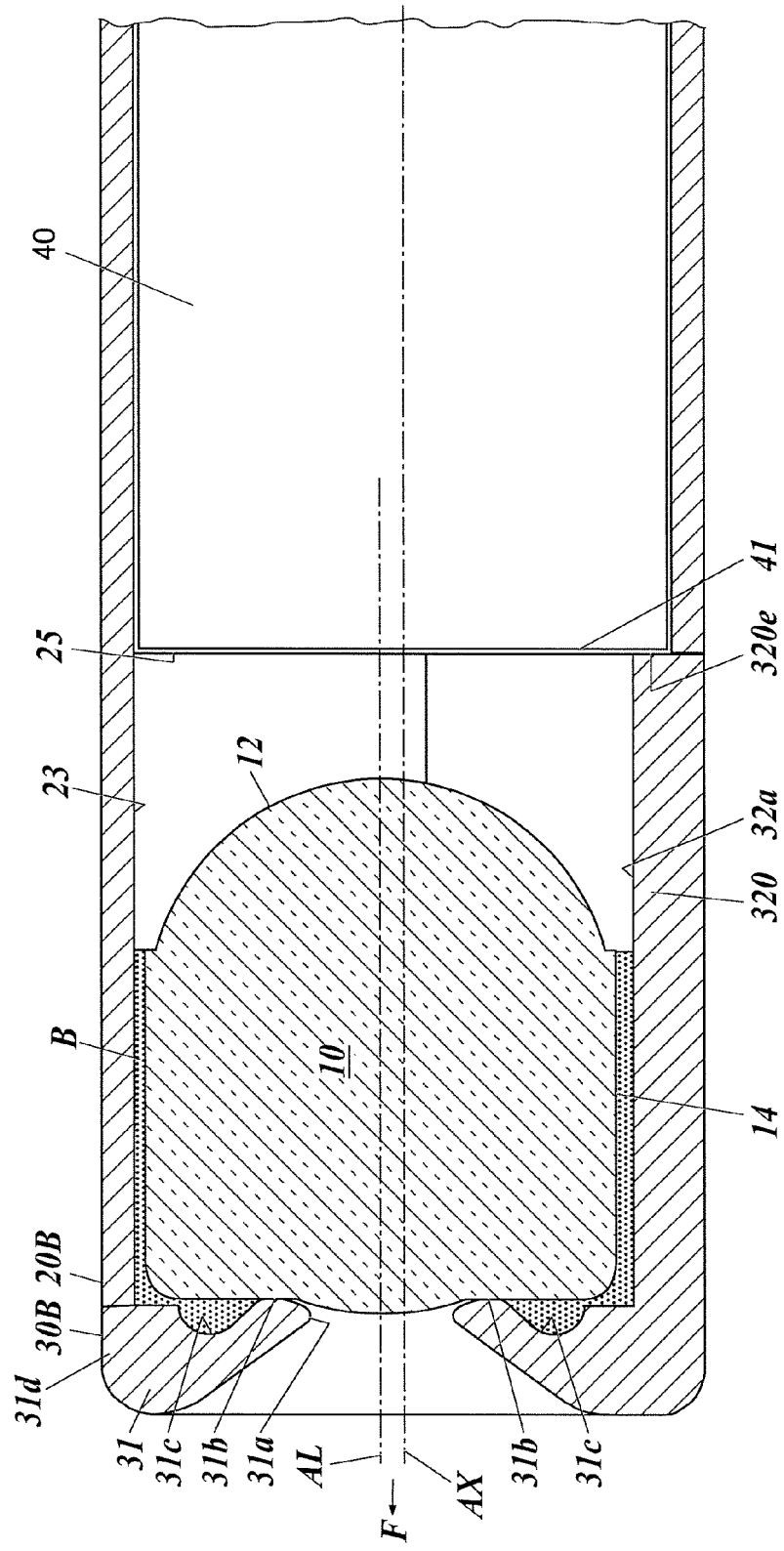
FIG. 10 is a longitudinal sectional view of the tip portion of the image obtaining unit including a lens barrel of the fourth embodiment of the present invention.

The lens base component employed in the present embodiment is shown in FIG. 9A and FIG. 9B.

A vertical groove 32g to store the gate edge 15 is formed in the arc shaped side wall portion 32A as shown in FIG. 9A, and a vertical groove 32h to store the gate edge 15 is formed in the arc shaped side wall portion 32B as shown in FIG. 9B.

With this, the lens can be embedded even if the gate edge 15 is left, the process to remove the gate edge 15 is not necessary, and the productivity is enhanced.

The vertical groove 32b is formed with the bottom of the groove remaining, and the vertical groove 32h is formed so as to divide the arc shaped side wall portion 32B into two.

Moreover, a vertical groove to store the gate edge 15 can be provided in the full circle side wall portion 33 of the second embodiment. When the vertical groove which divides the side wall portion into two is employed, obviously the side wall portion is no longer in a shape of a full circle.

In either case, it is preferable to provide the above vertical grooves on the side opposite to the side that the lens is shifted. This is to secure the space to store the gate edge 15.

Fourth Embodiment

Next, the fourth embodiment of the present invention is described.

According to the present embodiment, a portion of the cylinder body component 20 next to the outer side of the arc shaped side wall portion 32 shown in FIG. 1 is changed to belong to the arc shaped side wall portion 320 as shown in FIG. 10 and FIG. 11A to FIG. 11D.

Figure 11A:
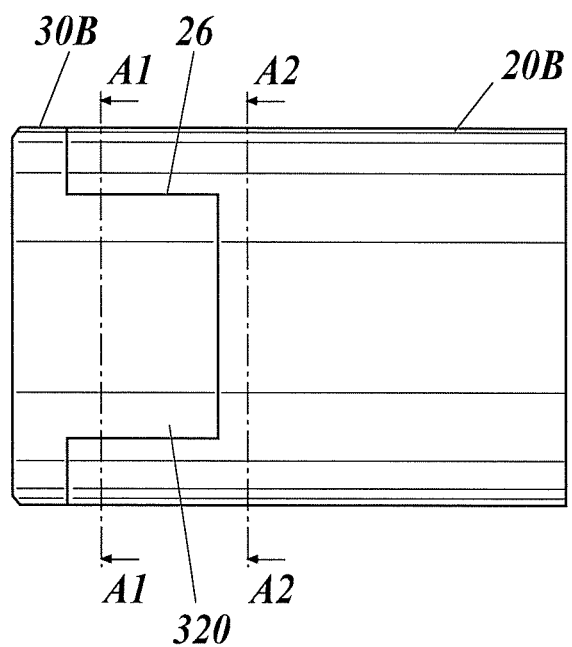
FIG. 11A is a side view of the lens barrel of the fourth embodiment of the present invention.
Figure 11B:
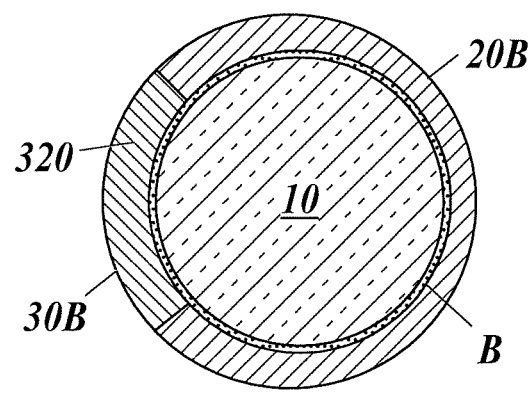
FIG. 11B is a cross sectional view along A1-A1 of the lens barrel of the fourth embodiment of the present invention.
Figure 11C:
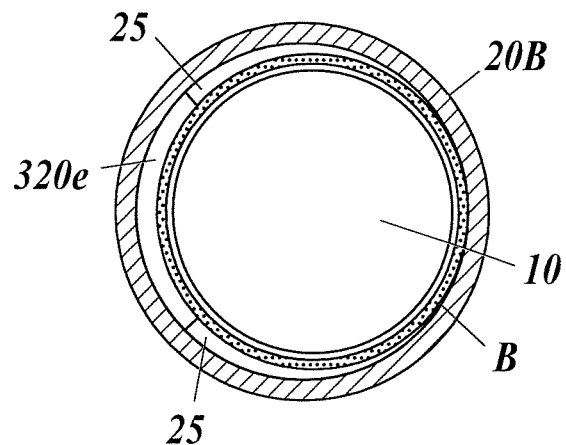
FIG. 11C is a cross sectional view along A2-A2 of the lens barrel of the fourth embodiment of the present invention.
Figure 11D:
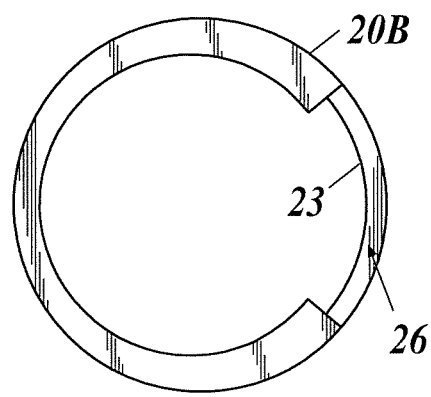
FIG. 11D is a tip surface view of a cylinder body component of the lens barrel of the fourth embodiment of the present invention.

As shown in FIG. 11A and FIG. 11D, the cylinder body component 20B includes a cutout portion 26 formed cut out from the tip surface. The arc shaped side wall portion 320 included in the lens base component 30B corresponds to the portion corresponding to the arc shaped side wall portion 32 of the first embodiment and the portion missing from forming the cutout portion 26 of the cylinder body component 20 formed as one. The former corresponds to the inner side portion of the arc shaped side wall portion 320 and the latter corresponds to the outer side portion of the arc shaped side wall portion 320.

Therefore, as shown in FIG. 10 and FIG. 11A to FIG. 11C, the outer side portion of the arc shaped side wall portion 320 fits into the cutout portion 26 and the cutout portion 26 is closed to compose the lens barrel of the present embodiment.

The inner side portion (portion exposed in FIG. 11C) of the upper surface 320e of the arc shaped side wall portion 320 composes the positioning surface which determines the position of direction of the axis AX of the tip surface 41 of the imaging unit or the imaging fiber 40 similar to the upper surface 32e of the first embodiment.

According to the present embodiment, the arc shaped side wall portion 320 can be made thick and the hardness can be secured.

A step surface 25 shown in FIG. 1, FIG. 6, FIG. 10 and FIG. 11C is a step surface which continues to the same surface as the positioning surface composed by the upper surface 32e of the first embodiment or the upper surface 320e of the present embodiment and is a portion composed inside the cylinder body component 20. The step surface 25 functions similarly as the positioning surface to determine the position of the direction of the axis AX of the tip surface 41 of the imaging unit or the imaging fiber 40. The step surface 25 is made with a small width compared to the positioning surface of the upper surface 32e or the upper surface 320e, and therefore can be omitted. When the step surface 25 is omitted, the entire inner circumferential surface 23 can be composed with the same inner diameter. Therefore, this is advantageous in that the cylinder body component 20 can be made easily.

INDUSTRIAL APPLICABILITY

The present invention can be used as the component of the endoscope with a small diameter and the method of assembling the above.

REFERENCE NUMERAL LIST 1 lens barrel
2 lens frame
10 lens
11 tip side optical surface
12 end side optical surface
13 tip surface
14 outer circumferential surface
15 gate edge
20 cylinder body component
21 tip opening
22 end opening
23 inner circumferential surface
24 tip surface
25 step surface
26 cutout portion
30 lens base component
31 tip base portion
31a opening
31b tip contact portion
31c groove
31d flange portion
32 arc shaped side wall portion
32a inner side surface
32b outer side surface
32c groove
32d through hole
32e upper surface
32g vertical groove
32h vertical groove
33 full circle side wall portion
33e upper surface
33f thinnest portion
40 imaging unit or imaging fiber
41 tip surface
100 image obtaining unit
320 arc shaped side wall portion
320e upper surface
AL lens central axis
AX central axis
B adhesive

The invention claimed is:

1. A lens barrel comprising:
a lens which images an image of a subject; and
a lens frame which holds the lens inside,
wherein,
the lens frame includes:
a cylinder body component with a structure opened at a tip and an end; and
a lens base component which fixes the lens and which is adhered and fixed to a tip opening of the cylinder body component to store the lens inside the cylinder body component;
the lens base component includes:
a tip base portion including an opening which exposes a tip side optical surface of the lens and an inner side surface which supports the lens in a surrounding portion of the opening; and a full circle or arc shaped side wall portion provided standing from the tip base portion in an axis direction;

the inner side surface of the side wall portion is formed along an outer circumferential surface of the lens;

the inner side surface and the outer circumferential surface are brought together and adhered to each other;

at least a portion of the upper surface of the side wall portion is provided in a position toward an end side separated from the far end of the lens to be exposed to the inside of the cylinder body component, comes into contact with a tip surface edge of a member with a larger diameter than the lens inserted from an end opening of the cylinder body component, and composes a positioning surface to determine a position of an axis direction of the member; and the lens is provided in a position shifted from a central axis of an inserting portion in which the member of the cylinder body component is inserted and the positioning surface is provided in a side opposite of the side that the lens is shifted, wherein the side wall portion is inserted in the cylinder body component;

the outer side surface of the side wall portion is formed along an inner circumferential surface of the cylinder body component; and the outer side surface and the inner circumferential surface are brought together and adhered to each other.

2. The lens barrel of claim 1, wherein, the side wall portion is formed in an arc shape in which a portion on the side that the lens is shifted is missing.

3. The lens barrel of claim 1, wherein, the tip base portion includes a flange portion projecting outward from the side wall portion in a radial direction in an outer circumferential portion; and the flange portion is in contact with a tip surface of the cylinder body component in a full circle.

4. The lens barrel of claim 1, wherein, a groove is formed in an outer side surface of the side wall portion, and the outer side surface is adhered to an inner circumferential surface of the cylinder body component by adhesive filled in the groove.

5. The lens barrel of claim 1, wherein, a cutout portion is formed cutting out the cylinder body component from a tip surface; and the side wall portion fits into the cutout portion to close the cutout portion.

6. The lens barrel of claim 1, wherein, a groove is formed in a portion surrounding a portion which supports a tip surface of the lens of an inner side surface of the tip base portion in a full circle, and the lens is fixed to the tip base portion by adhesive filled in the groove.

7. The lens barrel of claim 1, wherein, a through hole is formed on the side wall portion to go through to the inner side surface of the side wall portion, the inner side surface in contact with the outer circumferential surface of the lens.

8. The lens barrel of claim 1, wherein a gate edge formed in injection molding of the lens is left projecting from an outer circumferential surface of the lens, and a groove to store the gate edge is formed in the side wall portion.

9. An image obtaining unit comprising:

a lens barrel of claim 1, wherein, an imaging unit or an imaging fiber is inserted in the cylinder body component as the member, the imaging unit or the imaging fiber with an image input surface where an image imaged by the lens is input provided in a tip surface; and the imaging unit or the imaging fiber is held so that an outer circumferential surface is in contact with an inner circumferential surface of the cylinder body component in a full circle, and a tip surface edge comes into contact with the positioning surface to hold an interval with the lens in an axis direction.

10. A method for assembling a lens barrel according to claim 1, comprising:

adhering and fixing the lens to the lens base component; and after the above, adhering and fixing the lens base component to the cylinder body component.

11. A method for assembling an image obtaining unit according to claim 9, comprising:

adhering and fixing the lens to the lens base component, and then adhering and fixing the lens base component to the cylinder body component;

after the above, inserting the imaging unit or the imaging fiber in the cylinder body component and fixing the cylinder body component in a state where the tip surface edge is in contact with the positioning surface.

12. A method for assembling an image obtaining unit comprising a lens barrel, wherein the lens barrel comprises:

a lens which images an image of a subject; and a lens frame which holds the lens inside, wherein, the lens frame includes:

a cylinder body component with a structure opened at a tip and an end; and a lens base component which fixes the lens and which is adhered and fixed to a tip opening of the cylinder body component to store the lens inside the cylinder body component;

the lens base component includes:

a tip base portion including an opening which exposes a tip side optical surface of the lens and an inner side surface which supports the lens in a surrounding portion of the opening; and a full circle or arc shaped side wall portion provided standing from the tip base portion in an axis direction;

the inner side surface of the side wall portion is formed along an outer circumferential surface of the lens;

the inner side surface and the outer circumferential surface are brought together and adhered to each other;

at least a portion of the upper surface of the side wall portion is provided in a position toward an end side separated from the far end of the lens to be exposed to the inside of the cylinder body component, comes into contact with a tip surface edge of a member with a larger diameter than the lens inserted from an end opening of the cylinder body component, and composes a positioning surface to determine a position of an axis direction of the member; and the lens is provided in a position shifted from a central axis of an inserting portion in which the member of the cylinder body component is inserted and the positioning surface is provided in a side opposite of the side that the lens is shifted, wherein an imaging unit or an imaging fiber is inserted in the cylinder body component as the member, the imaging unit or the imaging fiber with an image input surface where an image imaged by the lens is input provided in a tip surface, wherein the imaging unit or the imaging fiber is held so that an outer circumferential surface is in contact with an inner circumferential surface of the cylinder body component in a full circle, and a tip surface edge comes into contact with the positioning surface to hold an interval with the lens in an axis direction, and wherein the method for assembling an image obtaining unit comprises:
- adhering and fixing the lens to the lens base component, and then adhering and fixing the lens base component to the cylinder body component; and
- after the above, inserting the imaging unit or the imaging fiber in the cylinder body component and fixing the cylinder body component in a state where the tip surface edge is in contact with the positioning surface.

\* \* \* \* \*